Feb. 8, 1955 E. S. BOERNER Plant Pat. 1,346
ROSE PLANT
Filed April 29, 1954
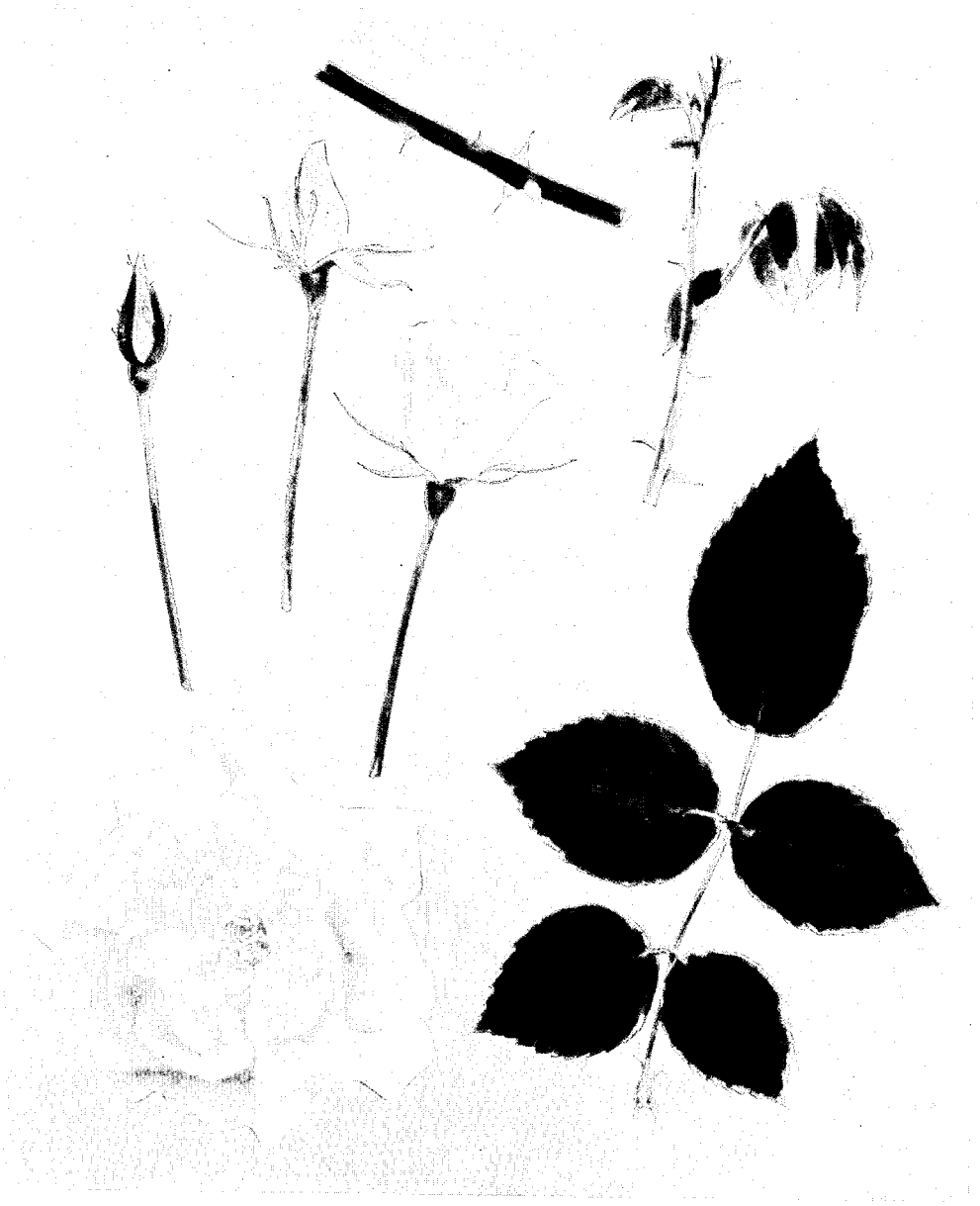
Inventor.
E. S. Boerner
By: Robb & Robb
Attorneys.

United States Patent Office

Plant Pat. 1,346

Patented Feb. 8, 1955

1,346

ROSE PLANT

Eugene S. Boerner, Newark, N. Y., assignor to Jackson & Perkins Company, Newark, N. Y., a corporation of New York Application April 29, 1954, Serial No. 426,619

1 Claim. (Cl. 47—61)

The present invention relates to a new and distinct variety of rose plant of the large-flowered polyantha class, which was originated by me by crossing the variety "Goldilocks" (Plant Patent No. 672) with the variety "Geranium Red" (Plant Patent No. 811).

The primary objective in making this cross was to intensify and accentuate the coloring of the flowers of the variety "Goldilocks," which normally bears flowers of Yellow general color tonality, while at the same time, transmitting to the flowers a stronger and more distinctive fragrance. These objectives were fully achieved, as evidenced by the distinctive Rose Red general color tonality of the flowers of my new variety, lightly overcast with Scarlet Red and showing a definite suffusion of Yellow in the lower half of the petals, together with a distinctive, strong, and very sweet Rose Geranium fragrance. In addition to these characteristics, my new variety is endowed with a vigorous, bushy habit of growth of the plant, along with foliage of rich, Dark Green color. The latter characteristics, taken together with the distinctive coloring and fragrance of the flowers of my new variety, represent a unique and desirable combination in a rose of this class, and definitely distinguish my new variety from its parents, as well as from all other varieties.

Asexual reproduction of my new variety by budding at Newark, New York, and also at Pleasanton, California, shows that the foregoing characteristics and distinctions come true to form and are established and transmitted through succeeding propagations.

The accompanying drawing shows typical specimens of the flowers, foliage and stems of my new variety in different stages of development, with the specimens depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed Parent.*—"Goldilocks."
*Pollen Parent.*—"Geranium Red."
Classification:
*Botanic.*—Large-flowered polyantha.
*Commercial.*—Floribunda.

FLOWER (Observations made from specimens grown outdoors at Newark, New York, in the early part of the month of August, and in the early afternoon.)

Blooming habit: Recurrent—continuous.
Bud:
*Size.*—Medium.
*Form.*—Ovoid; is not affected by wet or hot weather.
*Color.*—When sepals first divide—Spectrum Red, Plate 1, lightly overcast with Rose Red, Plate 12. When petals begin to unfurl—Scarlet Red, Plate 1, lightly overcast with Rose Red, Plate 12. When half blown: inside of petals—Scarlet Red, Plate 1, overcast with Peach Red, Plate 1, reverse of petals—Rose Red, Plate 12, lightly overcast with Scarlet Red, Plate 1 and with a suffusion of Salmon Orange, Plate 2 in the lower half of the petals.
*Sepals.*—Slightly branched; curl back when petals begin to unfurl. Color: inside—Kildare Green, Plate 31; outside—Bice Green, Plate 17.
*Calyx.*—Color—Light Elm Green, Plate 17. Shape—pear. Size—small. Aspect—smooth. Odor when rubbed—none.
*Peduncle.* — Length — short. Aspect — rough. Strength—Erect; slender. Color—Light Cress Green, Plate 31.
*Opening.*—Opens up well; is not affected by adverse weather conditions.

Bloom:
*Size.*—Large; average size when fully expanded—from 3 inches to 4 inches.
*Borne.*—Several together, and sometimes in irregular clusters.
*Stems.*—Medium length; strong.
*Form (when first open).*—High center to open. Permanence—retains its form to the end, but outer petals curl back.
*Petalage.*—Double (full but open center). Number of petals under normal conditions—from 25 to 30.
*Color.*—Center of flower—Scarlet Red, Plate 1, lightly overcast with Rose Doree, Plate 1 and with a suffusion of Deep Chrome, Plate 3 in the lower half of the petals. Outer petals—Begonia Rose, Plate 1, lightly overcast with Rose Doree, Plate 1. Base of petals (aiglet)—Lemon Yellow, Plate 4. Inside of petals—Rose Red, Plate 12, lightly overcast with Scarlet Red, Plate 1 and with a suffusion of Deep Chrome, Plate 3 in the lower half of the petals. Reverse of petals—Rose Doree, Plate 1, lightly overcast with Scarlet Red, Plate 1. General tonality from a distance—Scarlet Red, Plate 1, overcast with Rose Doree, Plate 1.
*Discoloration.*—General tonality at end of first day—Scarlet Red, Plate 1, lightly overcast with Rose Doree, Plate 1. Second day—Scarlet Red, Plate 1, overcast with Rose Doree, Plate 1. Third day—Rose Red, Plate 12, lightly overcast with Scarlet Red, Plate 1.
Petals:
*Texture.*—Thick; is not affected by wet or hot weather.
*Appearance.*—Inside—satiny. Outside—shiny.
*Form.*—Oval.
*Arrangement.*—Irregular.
*Petaloids in Center.*—Few; small.
*Persistence.*—Drop off cleanly.
*Fragrance.*—Strong. Nature—very sweet, Rose Geranium fragrance.
*Lasting Quality.*—On the plant—very long. As cut flower—very long.

GENITAL ORGANS

Stamens, anthers: Medium size; many; regular around styles. Color—Deep Chrome, Plate 3.
Stamens, filaments (threads)—Medium length. Color—Empire Yellow, Plate 4.
Pollen: Color—Pale Orange Yellow, Plate 3.
Styles: Columnar; uneven length; medium length; thin.
Stegmas: Color—Stray Yellow, Plate 16.
Ovaries: All enclosed in calyx.
Hips: None.
Seeds: None.

PLANT

Form: Bush.
Growth: Vigorous; upright; compact.
Foliage: 5 to 7 leaflets.
*Size.*—Medium.
*Quantity.*—Abundant.
*Color.*—New foliage: upper side—Maroon, Plate 1, with serrations of light Cress Green, Plate 31; under side—Carmine, Plate 1. Old foliage: upper side—Dark Dull Yellow-Green, Plate 32; under side—Light Hellebore Green, Plate 17.
*Shape.*—Oval pointed.
*Texture.* — Upper side — leathery; glossy. Under side—smooth.

*Ribs and veins.*—Ordinary.
*Edge.*—Serrated (saw-toothed).
*Serration.*—Both double and single; small.
*Leaf Stem.*—Color—Cress Green, Plate 31. Under side—rough.
*Stipules.*—Bearded; long.

Wood:
*New wood.*—Color—Courge Green, Plate 17. Bark—smooth.
*Old wood.*—Color—Yew Green, Plate 31. Bark—smooth.

Thorns:
*Thorns.*—Quantity: On main stalks from base—ordinary; on laterals from stalk—Many. Form—narrow base; medium length; straight. Color (when young)—Spectrum Red, Plate 1. Position—irregular.

*Prickles.*—Quantity: on main stalks—none; on laterals—none.
*Short needles.*—Quantity; on mainstalks—none; on laterals—none.

I claim:

A new and distinct variety of Rose plant of the large-flowered polyantha class, substantially as herein shown and described, particularly characterized as to novelty by the distinctive color of its flowers, the distinctive, strong and very sweet Rose Geranium fragrance of its flowers, the vigorous and bushy habit of growth of the plant, and the rich, Dark Green color of its foliage.

No references cited.